United States Patent [19]
Andley et al.

[11] Patent Number: 5,643,782
[45] Date of Patent: Jul. 1, 1997

[54] IMMORTALIZED EPITHELIAL CELL LINES

[75] Inventors: Usha P. Andley; Timothy P. Fleming, both of Ballwin, Mo.

[73] Assignee: Washington University in St. Louis, St. Louis, Mo.

[21] Appl. No.: 110,726

[22] Filed: Aug. 23, 1993

[51] Int. Cl.$^6$ ............... C12N 5/00; C12N 5/02; C12N 1/00

[52] U.S. Cl. ............ 435/371; 435/172.1; 435/172.2; 435/948; 435/346; 435/378

[58] Field of Search ............... 435/240.2, 240.21, 435/240.26, 172.1, 172.2, 173.1, 320.1, 948

[56] References Cited

U.S. PATENT DOCUMENTS 4,707,448  11/1987  Major ........................... 435/240.25
4,885,238  12/1989  Reddel et al. .................. 435/29

OTHER PUBLICATIONS

Rhim, J.S., Anticancer Research, 9:1345–1366 (1989).
Ueda et al., Cell Structure & Function, 16(6), p. 563 (Dec. 1991).
Kahn et al., Assoc. for Research in Vision & Opthalmology, Annual Meeting—Invest. Opthal. & Visual Sci., 33(4), p. 1176 (1992).
Rhim et al., Science, 227:1250–1252 (Mar. 8, 1985).
Kahn et al, Invest. Opth. & Vis. Sci 34(12) pp. 3429–3441 (Nov. 1993).
Araki et al., Invest. Ophth. & Vis. Sci 34(9) pp. 2665–2671 (Aug. 1993).
Rhim et al., Leukemia, 2(12 Suppl) pp. 151S–159S (Dec. 1988).
Andley et al., Invest. Opth. & Vis. Sci 35(7), pp. 3094–3102 (Jun. 1994).
Trevithick et al, Invest. Opth. & Vis. Sci, 0(Suppl.) p. 48 (1979).
Miller et al., Dev. Growth Differ 21(1), pp. 19–28 (1979).
Robertson et al, Invest. Ophthalmol. Visual Sci, 28 (3 Suppl) p. 13 (1987).
Reddy, V.N., et al., "Crystallins and their Synthesis in Human Lens Epithelial Cells in Tissue Culture," *Exp. Eye Res.* (1988) 47, 465–478.
Arita, T. et al., "Enhancement of Differentiation of Human Lens Epithelium in Tissue Culture by Changes in Cell–Substrate Adhesion," *Inv. Ophthal. & Visual Science*, (1990) 31:11, 2395–2404.
Nagineni, C.N. et al., "Lens Fiber Cell Differentiation and Expression of Crystallins in Co–cultures of Human Fetal Lens Epithelial Cells and Fibroblasts," *Exp. Eye Res.* (1992) 54, 193–200.
Reddy, V.N. et al., "Study of Crystallin Expression in Human Lens Epithelial Cells During Differentiation in Culture and in Non–lenticular Tissues," *Exp. Eye Res.* (1991) 53, 367–374.
Gwon, A., et al., "Lens Regeneration in New Zealand Albino Rabbits After Endocapsular Cataract Extraction," *Inv. Ophthal. & Visual Science*, (1993) 34:6, 2124–2129.
Nagineni, C.N., et al., "Human fetal lens epithelial cells in culture: an in vitro model for the study of crystallin expression and lens differentiation," *Current Eye Res.*, (1989) 8:3, 285–291.
Worgul, B.V., et al., "Cortical Cataract Development—An Expression of Primary Damage to the Lens Epithelium," *Lens & Eye Tox. Res.*, (1989) 6(4), 559–571.

*Primary Examiner*—Michael G. Wityshyn
*Assistant Examiner*—Blaine Lankford
*Attorney, Agent, or Firm*—Nath & Associates; Gary M. Nath; Todd L. Juneau

[57] ABSTRACT

An immortalized epithelial lens cell line obtained from human lens epithelial cells infected with hybride adenovirus/SV40 (Ad12-SV40), and methods for making and using the cell line are disclosed.

8 Claims, 6 Drawing Sheets

IMMORTALIZED EPITHELIAL CELL LINES

STATEMENT OF RIGHTS

The U.S. Government has a paid-up license in this invention and the right in limited circumstances to require the patent owner to license others on reasonable terms as provided for by the terms of Grant No. EY 05681 awarded by National Institute of Health.

BACKGROUND OF THE INVENTION

(1) Field of the Invention

The invention relates to the formation of immortalized cell lines and more particularly to immortalized epithelial cell lines infected with a hybrid SV40 adenovirus, as well as to methods of preparing the cell lines and uses therefore.

(2) Description of the Related Art

The establishment of lens epithelial cells in tissue culture is of considerable importance not only for the study of the problem of cell differentiation, but also is valuable for studying the etiology of primary and secondary cataract. It is also of interest as a progenitor of lens fibers in vivo and because information concerning the regulation of their growth and gene expression is limited. Although there have been a number of studies concerning cell lines of animal lens epithelial cells in culture, attempts to grow human lens epithelia have only been modestly successful.

It is well known that lens epithelial cells undergo a developmental transition into fiber cells of the lens cortex, a process characterized by distinct biochemical changes such as the synthesis of fiber-specific protein, $\beta$ and $\gamma$-crystallins and morphological changes such as cell elongation, loss of cellular organelles and disintegration of the nucleus. The lens epithelium is located on the anterior surface of the lens immediately beneath the capsule and is thought to play a pivotal role in the development and progression of human cataracts, particularly those caused by exogenous mutagens. Data from experimentally induced cataracts and clinical experience suggest that primary damage to the genome of the epithelial cells, mediated by abnormal differentiation to lens fiber cells is collectively expressed as a cataract. See Worgul B. V., Merriam G. R. and Medvedovsky C. "Cortical cataract development—an expression of primary damage to the lens epithelium." *Lens Eve Tox Res.* 1989;6:559–571.

Early attempts to culture human lens epithelial cells were not very successful, due to their low proliferative ability in vitro, which decreased with age of the tissue. See, for example, Tassin J., Malaise E. and Courtois Y. "Human lens cells have an in vitro proliferative capacity inversely proportional to the donor age." *Exp Cell Res.* 1979; 123:388–392; Hamada Y. and Okada TS. "In vitro differentiation of cells of the lens epithelium of human fetus." *Exp Eye Res.* 1978; 26:91–97; Reddan J. R., McGee S. J., Goldenberg E. M., and Dziedzic. "Both human and newborn rabbit lens epithelial cells exhibit similar and limited growth properties in tissue culture." *Curr Eye Res.* 1982/1983; 2:399–405; and Jacob T. J. C., "Human lens epithelial cells in culture." *Exp Eye Res.* 1987; 45:93–104.

More recently, human lens epithelial cells have been cultured using fetal or infant lens epithelial explants. These efforts demonstrated the presence of crystallins but revealed their decreased production after several cell passages. See, Reddy V. N., Arita L. T., Zigler J. S., Jr. and Huang Q. L., "Crystallins and their synthesis in human lens epithelial cells in tissue culture." *Exp Eye Res.* 1988; 47:465–478; and Arita T., Lin L-R and Reddy V. N., "Differentiation of human lens epithelial cells in tissue culture." *Exp Eye Res.* 1988; 47:905–910.

Primary cultures of infant and fetal cells have been successfully grown and cultured through at least three (3) passages with the consistent formation of a monolayer with population doublings of up to 12 in culture. See Nagineni C. N., and Bhat S. P., "Human fetal epithelial cells in culture: an in vitro model for the study of crystallin expression and lens differentiation." *Curr Eye Res.* 1989; 8:285–291. These cells have been shown to express $\alpha$, $\beta$ and $\gamma$-crystallins characteristic of epithelial cells undergoing differentiation into fibers, synthesize the capsule in vitro, and can undergo cell differentiation into fiber like cells of lentoids on low protein-binding surfaces or in co-cultures of lens epithelial cells and ciliary fibroblasts. Despite these advances, the practical utility of human lens epithelial cells is hindered by the limited availability of infant and fetal lenses, diminished in vitro growth after 4–6 population doubling levels (pdls) in cell culture, the lack of continuous cell lines, and the long proliferation times required to obtain a sufficient number of cells for use as a model for studying cell differentiation and the etiology of cataract.

Further studies have been undertaken with virus-transfection of mammalian cells with transforming virus to immortalize cells in vitro. Zeitlin PL., Lu L., Rhim J., Cutting G., Stetten G., Kieffer K. A., Craig R. and Guggino W. B., "A cystic fibrosis bronchial epithelial cell line: immortalization by Adeno-12-SV40 infection." *Am. J. Respir. Cell Mol. Biol.* 1991. 4:313–319; Hoffman M-C, Narisawa S., Hess R. A. and Millan J. L., "Immortalization of germ cells and somatic testicular cells using the SV40 large T antigen." *Exp Cell Res.* 1992, 201:417–435; and Bartek J., Bartkova J., Kyprianou N., Lalani E-N., Staskova Z., Shearer M., Chang S. and Taylor-Papadimitrou J., "Efficient immortalization of luminal epithelial cells from mammary gland by introduction of similar virus 40 large tumor antigen with a recombinant retrovirus." *Proc. Natl. Acad. Sci. USA* 1991; 88:3520–3524. Limited success has been reported with bovine and rat lens epithelium. Miller G. G., Blair D. G., Hunter E., Mousa G. Y. and Trevithick J. R., "Differentiation of rat lens epithelial cells in tissue culture (III). Functions in vitro of a transformed rat lens epithelial cells line". *Develop Growth an Differ.* 1979;21:19–27. Bovine lens epithelial cells have also been conditionally immortalized by a temperature-sensitive mutant; of the SV40 virus and rat lens epithelial cells have been transformed using rous sarcoma virus, retaining partially differentiating function as shown by $\beta$-crystallin synthesis. No immortalized cell lines exist, however, for the human lens epithelium. However, the availability of such a cell line would greatly enhance the study of human lens epithelial physiology, and may aid in the design of drugs that inhibit both primary and secondary human cataracts. Thus, the availability of a cell line which maintains the normal differentiating functions of the lens epithelial cells would be of practical importance in the study of cataractogenesis and agents that inhibit cataract.

SUMMARY OF THE INVENTION

The present invention relates to the formation of immortalized cell lines and more particularly to immortalized human lens epithelial cells using a hybrid adenovirus (Ad12-SV40) to maintain propagation of the cells in vitro. The immortalized human lens epithelial cells can be maintained in culture for at least 23 passages and over 55 population doublings, with no diminution in proliferative capability. Furthermore, it was unexpectedly discovered that these cells still synthesize $\beta$ and $\gamma$-crystallins as monitored by immunoblot assay, indicating that the immortalizing event has not altered the cells normal differentiating function. These cells may be an important model system for studying human lens-specific physiology, and to investigate the role of the lens epithelium in cataract formation.

In one aspect the invention involves the formation of an immortalized cell line, which comprises a tissue cell line infected with a hybrid adenovirus/SV40 which propagates in vitro.

In another aspect, the invention involves a cell culture capable of expressing β-crystallin, γ-cystallin and mixtures thereof obtained by infecting epithelial cells with an expressing vector of a hybrid adenovirus/SV40.

A further embodiment involves a method for producing an immortalized cell line, which comprises culturing an epithelial cell line with a hybrid adenovirus/SV40 to form an immortalized cell line capable of propagating in vitro; and collecting the immortalized cell line.

Additional embodiments of the invention involve antibodies immunoreactive with the immortalized cell line; peptides produced from the immortalized cell line and particularly peptides selected from the group consisting of βH-crystallins, and γ-crystallines (β5-crystallins), γS-crystallins, γC-crystallins, γD-crystallins and mixtures thereof.

Also included as a further aspect of the invention is a method for assaying lens inhibitory drugs, which comprises reacting the drugs with an immortalized epithelial cell line and determining the reactivity of the drugs on primary and secondary cataract formation, as well as a diagnostic assay which comprises as an essential component the immortalized epithelial cell line. Another embodiment involves the formation of cell lines for the study of cataractogenesis.

DESCRIPTION OF THE PREFERRED EMBODIMENTS

The human lens is a unique system for examining the relationship between gene expression and differentiation since populations of quiescent, dividing, differentiating and terminally differentiated cells are spatially segregated. It has been suggested that damage to the genome of lens epithelial cells by exogenous agents such as UV radiation, or other forms of oxidative stress may initiate or potentiate cataract formation. It is therefore important to investigate the physiology of the normal human lens epithelium and study its response to cataractogenic agents. These studies have been hindered by the lack of human lens epithelial cell lines that provide a homogeneous population of cells for the study of human lens specific functions such as expression of crystallin genes.

The present invention relates to the unexpected discovery of a human cell line with the capability to propagate indefinitely in long-term culture by the incorporation of the SV40 large T antigen into the genome of lens epithelial cells. These cell line have a stable epithelial morphology and continue to produce lens β and γ-crystallins, two proteins that are characteristic of lens cell differentiation in vivo and have been identified as β-5 and γD in the B-3 cell lines which has been deposited at the American Type Culture Collection, Rockville, Md. 20852, USA, on Jul. 27, 1993, as "cell line from human infant lens epithelium B-3", ATCC No. CRL 11421, in accordance with the Budapest Treaty.

Immunoprecipitation and SDS-PAGE tests suggest that the immortalized cells synthesize a β-crystallin polypeptide of molecular weight 24 kD, and a γ-crystallin of molecular weight 21 kD. β-Crystallins isolated from human lens fibers contain two polypeptides of molecular weights 24 and 26 kD, and the human monomeric fraction contains three polypeptides of molecular weights 24, 21 and 19 kD, corresponding to γS, γC and γD-crystallins, respectively. It is believed that the 24 kD protein of the immortalized human lens epithelial cells that immunoprecipitated with the βH-crystallins antibody is β5-crystallin and the 21 kD protein immunoprecipitated by the γ-crystallin antibody is γC-crystallin.

The human lens epithelial cell lines prepared by the present invention are capable of expressing endogenous crystallin genes while retaining the capability to propagate indefinitely in short population doubling times by immortalization with a virus. These cell lines present an important model for the study of human lens epithelial cell differentiation and its pathological manifestations in cataract and other disease states. These cells are useful for the assay of inhibitory drugs to prevent primary and secondary cataract formation, eye-related toxicology studies, and development of specific cell markers and immunodiagnostic tests useful for the clinical assessment of cataract development.

It is known that much of the landmark work in the study of mammalian genes came from working with tumor viruses. Tumor viruses infect mammalian cells, insert their own genetic material, and hijack the cellular biosynthetic machinery to manufacture more viruses. Often viral multiplication kills the cell. Sometimes the presence of tumor virus genes permanently alters the growth properties of an infected cell, transforming it into a tumor cell. Tumor viruses attracted the attention of researchers for several compelling reasons. Their genomes, which programs both viral life cycle in cells and the structural components of the virus itself, are often astonishingly small—the smallest DNA tumor viruses comprise a handful of genes packed into only 5000 bp. Within this small stretch of DNA lies the information for switching viral genes on and off in an ordered fashion, for replicating the vital genome, for assembling new virus particles, and for converting a normal cell into a cancer cell. Before recombinant DNA, these viruses, which could be purified in large quantities provided the only source of purified genetic material—DNA for some viruses, RNA for others—that functioned in mammalian cells.

The earliest gene transfer experiments were done with DNA tumor viruses such as the monkey tumor virus SV40, viruses whose genes are encoded in DNA just as cellular genes. DNA was isolated from purified viruses and introduced into cultures of uninfected cells. These cells eventually produced fully infectious viruses. This DNA-mediated transfer of infectious virus was dubbed transfection, to distinguish it from infection, the natural route of entry for viruses.

Applicants have unexpectedly discovered a hybrid method that uses infection to get DNA into cells and a viral protein to replicate it once inside to render the cells immortal and produce the β and γ-crystallin proteins. The mode of action, while not completely known, appears to involve the integration of a hybrid adenovirus/SV40, namely AD12-SV40 into the cell line. The cells then produce the viral T antigen protein which triggers replication of the viral DNA by binding to the cells DNA sequence.

In this way, an immortalized cell line is produced which comprises a tissue cell line infected with a AD12-SV40 which propagates in vitro. The preferred cell line is lens epithelial cells whereas the preferred hybrid adenovirus/SV40 is Ad12-SV40. The immortal cell lines are characterized by their ability to synthesize β-crystallins, and γ-crystallins and mixtures thereof and has been identified as B-3. Particular proteins having mean average molecular weights between 20–30 kD have been identified which react with antibodies to βH-crystallins and γ-crystallins.

Furthermore, the cell line produces a polypeptide having a 24 kD molecular weight material which appears to be β5-crystallin. Other peptides having molecular weights of 24, 21 and 19 kD are present in the human lens fibers produced which correspond with γS-crystallins, γC-crystallins and γD-crystallins. Accordingly, the invention provides a way to produce a peptide selected from the group consisting of βH-crystallins, γD-crystallins, γ5-crystallins, γS-crystallins and mixtures thereof, which may be isolated and purified for further use.

The invention also provides a novel, and simple immunoassay test system especially adapted for the detection and determination of a component of an antigen-antibody reaction. While the test protocol is not critical, any conventional tagging means, such as EIA, ELISA, RIA, may be used as well as conventional assays, such as straight assays, sandwich assays and sequential assays. The general principle of one procedure uses as a test reagent a given amount of one component of said reaction bound to the surface of a solid carrier, and as a second reagent, a given amount of the same component covalently linked to an enzyme. A diagnostic test for the detection and determination of the component of an antigen-antibody reaction can then be formed comprising an antibody to the immortal cell line bound to a solid carrier, a substance having the same immunological properties as the antibody linked to an enzyme or other marker (biotin-avidin and so forth) and optional binding partner of the component to be determined. Optional stabilizers may also be present to stabilize the antibodies during storage and/or testing procedures.

It has been found that antibodies can be conventionally produced to the novel immortal cell lines which are both monoclonal and polyclonal. Preferred monoclonal and polyclonal antibodies couple with the hybrid adenovirus present in the cell line, with the immortal cell line or proteins produced by the cell lines. Such antibodies as well as commercially available antibodies can be used in the immunoassay test systems of this invention, either alone or in combination.

A particularly preferred assay would involve assaying lens inhibitory drugs to determine their effect upon the lens tissue. A preferred procedure would involve reacting the active drugs to be tested with the epithelial immortalized cell line and determining the reactivity of the drugs on primary and secondary cataract formation. Such a testing protocol or assay procedure can be used for screening experimental drugs prior to use and for testing drugs for use with the eye for eye related taxocology. The invention also contemplates a method for assaying cytotoxicity of polymer coatings on intraoccular lenses.

The following examples are given to illustrate the invention, but are not to be limiting thereof. All percentages given throughout the specification are based upon weight unless otherwise indicated. All peptide molecular weights are based on mean average molecular weight unless otherwise indicated.

EXAMPLES

Primary cultures

Human lenses were obtained within 24 hrs. from 5–12 month old patients who underwent treatment for retinopathy of prematurity. A small cut was made in the posterior capsule of the lens, the free edge was grasped with forceps and the capsule with attached epithelium was cut into 2 or 3 fragments and each fragment was placed in a separate dish. The milliliters of minimum essential medium (MEM by Sigma) containing 20% fetal calf serum (by Sigma) and 50 µg/ml gentamicin were added to the culture. The cultures were maintained at 37° C. in a water-saturated air atmosphere containing 5% $CO_2$. Medium was changed twice weekly. The cells were routinely examined using a phase-contrast microscope.

Vital infection

After the primary cultures achieved confluence, the cells were subcultured using Trypsin-EDTA according to conventional procedures. See, for example, R. Ian Freshney. "Culture of animal cells. A manual of basic technique"; Chapter 10, —132–134. John-Wiley, New York (1987), which is incorporated herein by reference in its entirety. The secondary cultures were passaged again to confluence, into 100 mm plates. At 60% confluence, cells in the tertiary culture were infected with a 1:10 dilution of Ad12-SV40, diluted with culture medium MEM (minimum essential medium by Sigma) and incubated for 24 hours. At this time, the culture medium MEM containing 20% fetal bovine serum was removed, and 10ml fresh medium MEM containing 20% fetal bovine serum (FBS) was added to the cultures. Cells were allowed to grow for one week in a water-saturated air atmosphere containing 5% $CO_2$ and subcultured. After each passage, 24 hour collections of the culture medium were assayed for viral activity by a highly sensitive plaque assay.

Proliferation of immortalized cells

To determine the proliferative ability of the infected cells, 50,000 cells were plated in 60 mm plates (standard tissue culture-treated corning plates), 3 replicates for each time point, and the number of cells were counted using a Coulter counter. The growth assay was done over a period of 10 days, at which time the cultures were confluent.

Population doubling levels (pdl). To calculate pdl, the following equation was used:

$$N_f/N_o = 2^x$$

where x=number of population doublings, $N_f$=final number of cells and $N_o$=number of cells seeded into the plate initially. x=log $(N_f/N_o)$/log 2. After each passage, x was added to the previous population doubling level to get the new pdl.

Immunohistochemistry

Cells were plated in 24 well plates, grown to 60% confluence, and fixed with 1 ml of 70% ethanol for 15 minutes. After the addition of 200 µl of 0.05M Tris-Cl, pH 7.4, cells were incubated with the primary antibody (monoclonal mouse IgG for SV40 T antigen, Onocogene Science, Uniondale, N.Y.) at a dilution of 1:20 wash buffer for 1 hour. After 3 washes with wash buffer, cells were incubated with a biotin-labelled secondary antibody (rabbit anti mouse IgG from Dakopatts, Denmark) for 15 minutes at room temperature. Cells were then washed with wash buffer, incubated with avidin-peroxidase for 1.5 minutes, washed 3 times with wash buffer, and treated with freshly prepared substrate (diaminobenzidine) for 15 minutes. After extensive washing, cells were hydrated in wash buffer (0.05 M Tris. Cl., pH 7.4) and observed in a phase-contrast microscope.

SDS-PAGE and immunoblotting

Cells were lysed at 4° C., centrifuged at 10,000 g and the supernatants treated with the primary antibody. The cells immunoprecipitated using recombinant Protein G coupled to Agarose beads and the immune complexes were collected by centrifugation, washed with lysis buffer and suspended in 200 µl of SDS-PAGE buffer containing 50 mM-Tris-Cl, pH 6.8, 2% SDS, 1% 2-mercaptoethanol, 10% glycerol and 0.1% bromophenol blue. Electrophoresis was performed using 10% acrylamide gels according to Laemmli. See Laemmli U. K., "Cleavage of Structural Proteins During the Assembly of the Head of Bacteriophase T4. *Nature* 1970; 227:680–685 incorporated herein by reference. After immunoblotting on nitrocellulose membranes, the blots were probed with $^{125}$I-labelled Protein A.

Polyclonal antibodies for the crystallins were prepared by immunizing rabbits with purified calf lens βH-crystallin using conventional procedures. Antibody to γ-crystallin was obtained by immunizing rabbits with the monomeric protein fraction from infant human lenses using conventional procedures. The antibodies were isolated and purified from primary rabbit serum from animals infected with Calf βH or γ or human monomeric protein.

Results

Figure 1:
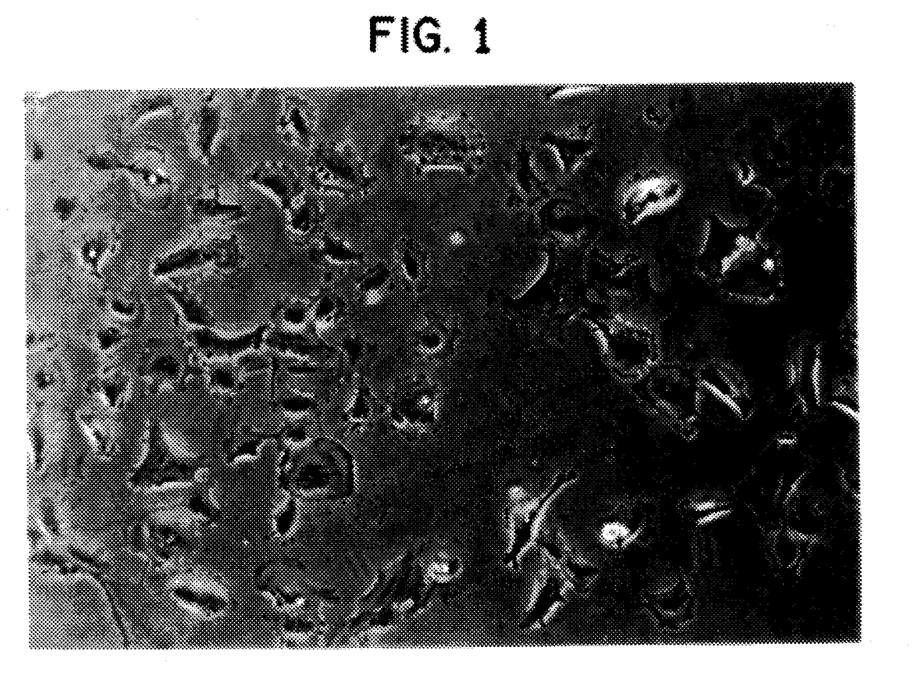
FIG. 1 is a photomicrograph of infant human lens epithelial cells.

Capsule-epithelium fragments obtained from infant human lenses attached to the culture dish, and cell outgrowth was evident within 3 days after the initiation of the primary cultures. The primary cultures were allowed to grow to confluence and subcultures (1:2) for two passages. FIG. 1 shows that the cells maintain a typical epithelial morphology after the first passage.

Figure 2:
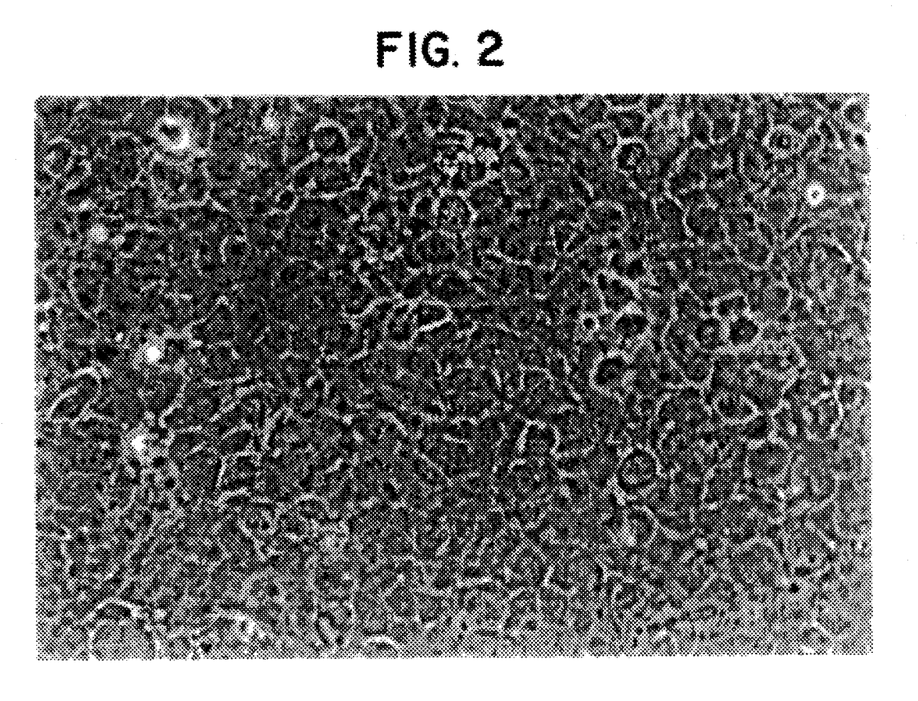
FIG. 2 is a photomicrograph of lens epithelial cells after infection with a hybrid adenovirus (Ad12-SV40).

Cells were then infected with the AD12-SV40 virus typically after a second passage achieved 60% confluence. The passage at which the cultures were infected did not appear to affect their immortalization. One week after virus infection, with adenovirus/SV40; population doubling level (pdl)=1.9, the infected cells continued to propagate to confluence, but the noninfected cultures showed diminished growth and failed to achieve confluence. Virus-infected cells ceased to produce intact virus in culture supernatants after 6–7 passages as shown by a plaque assay. Infected cells maintained their epithelial morphology and continued to grow to confluence as shown in FIG. 2. (Confluent monolayer of cells at passage 7 after virus infection, day 3 of culture; number of cells initially plated, n=6.6×10$^5$, pdl=15.6.) Cell cultures continued to maintain epithelial cell morphology in passage 8, second day of culture, and exhibited areas that were translucent and may be 'lentoids'. Non-confluent regions of the culture were also dense and translucent (passage 19, pdl=41.6, n=2.4×10$^5$). Some areas of the culture showed extensive aggregation of cells which were translucent, notably in cultures older than one week. Freezing the cells using 95% fetal calf serum and 5% DMSO using standard techniques did not alter cell viability.

Figure 3:
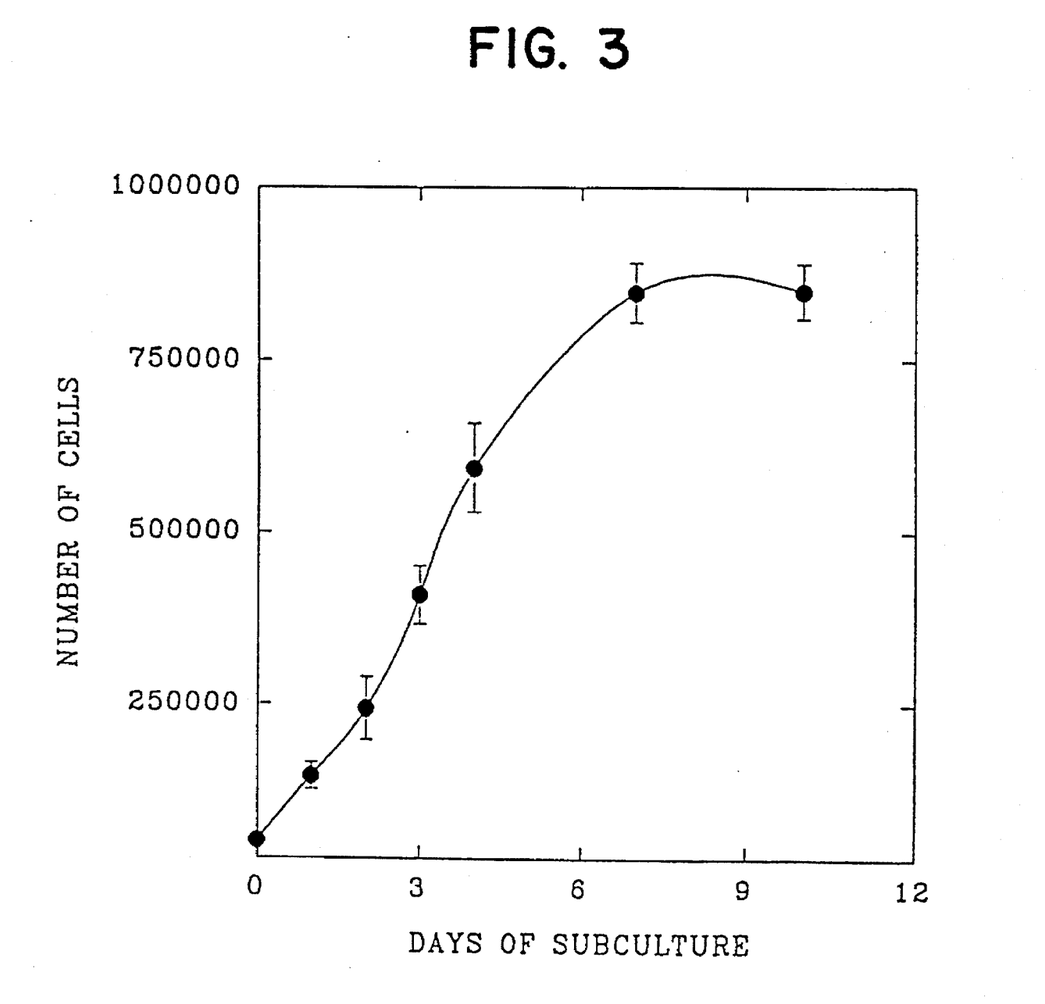
FIG. 3 is a growth curve for the cell line infected by the virus.

Cells were routinely subcultured after they reached confluence (about 7 days). The growth potential of the virus-infected cells was studied by plating 5×10$^4$ cells in 60 mm culture dishes incubated in MEM containing 20% FCS and the number of cells on days 1–10 was determined. FIG. 3 shows the growth curve for the virus infected cells in passage 7. Cells in passage 7 (pdl=15.6) were enzymatically removed from the plates. The total number of cells was determined at specific times. (Mean±SEM, n=3). The cells achieved four population doubles on day 7, and did not exhibit a decrease in growth potential at passage 22. These cultures have achieved population doubling levels of 40–50 and show no diminution of proliferation as a function of population doubling levels.

Figure 4:
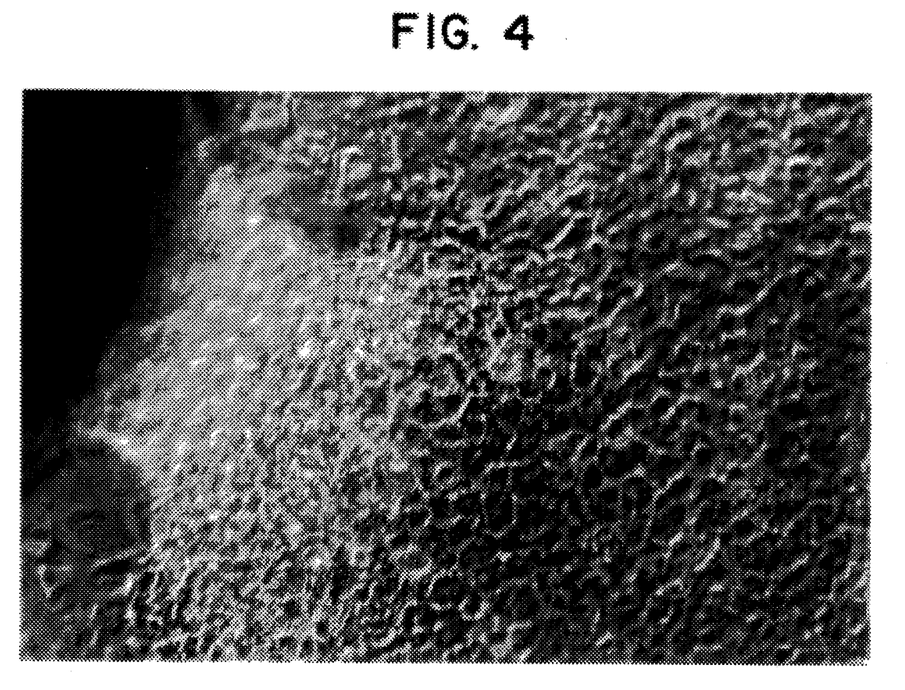
FIG. 4 is a photomicrograph of immortalized cells after 19 passages.

The effect of long-term culture on virus-transfected cells was studied with the results shown in FIG. 4, which are phase contrast micrographs of virus-infected lens epithelial cells in passage 19 after 30 days in culture. The monolayer cells begins to detach from the edges of the culture dish. Upon subculture, cells outgrow from the sheets to form a monolayer on plate coated with 2 µg/cm$^2$ fibronectin (Pdl=41.6). These sheets of cells were viable, and when removed from the plates and placed in fresh medium showed renewed attachment to the plate. The reattached cells continued to propagate into confluent cultures.

Figure 5:
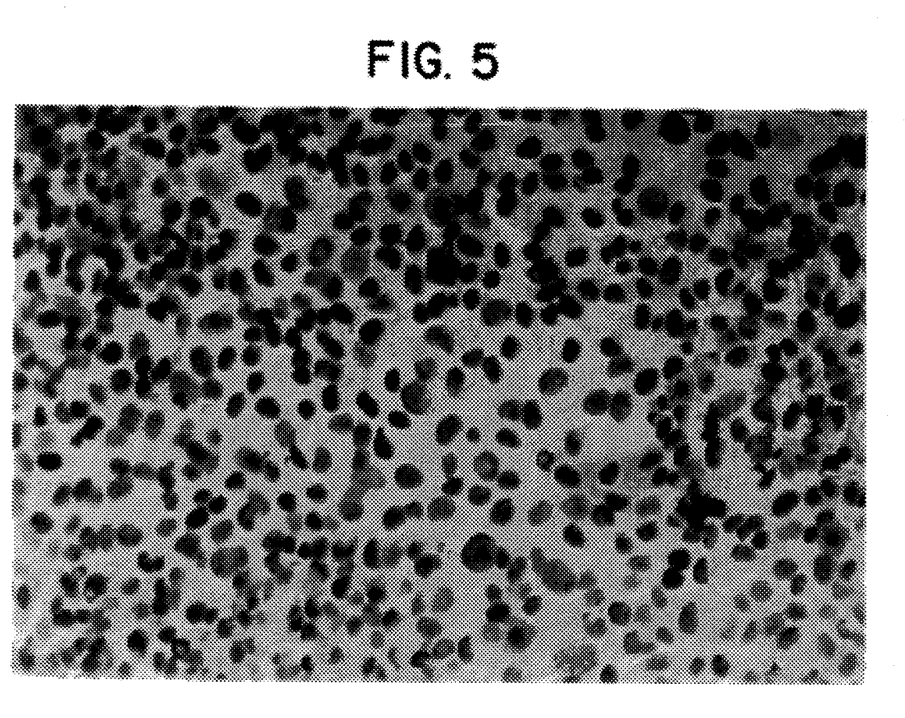
FIG. 5 is a photomicrograph of the mammalian SV40 antibodies to large T antigen immunoreactive to an immortalized cell line.
Figure 6:
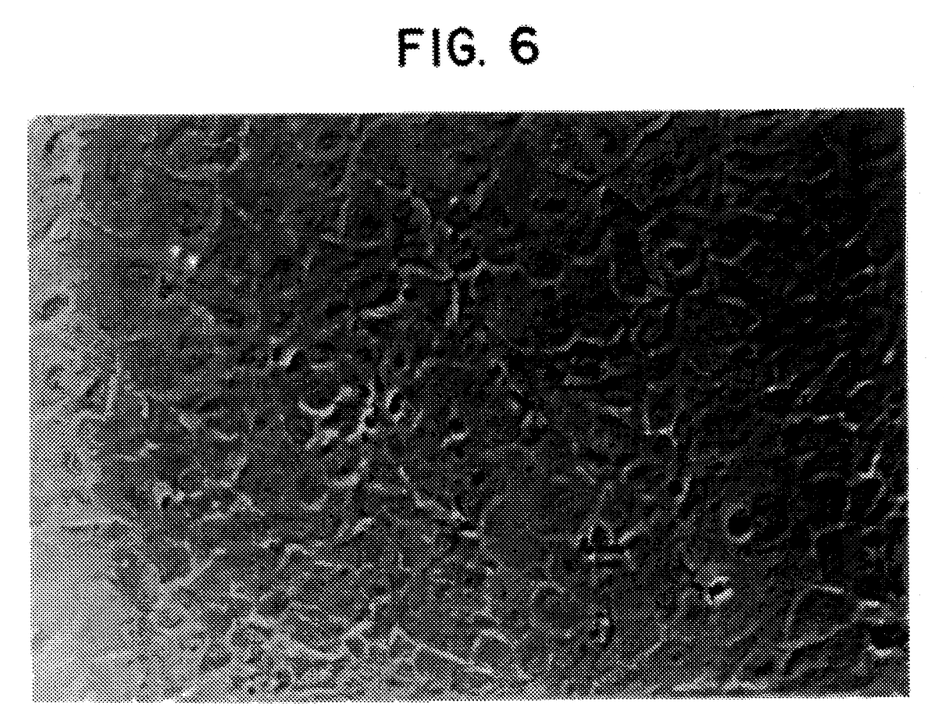
FIG. 6 is a photomicrograph of control uninfected cells treated with monoclonal antibody to SV40 large T antigen.

In FIG. 5, the immunohistochemistry of cultured lens epithelial cells using a mouse monoclonal primary antibody to SV40 large T antigen is demonstrated. Nuclear staining in the virus-infected cells indicates that the immortalized cells are T antigen-positive. Nearly 100% of the proliferative cells in the confluent monolayer are T antigen positive, indicating that the entire surviving population of cells contains the viral genome responsible for proliferation. Control cells without virus transfection treated with the monoclonal antibody showed faint cytoplasmic staining in the cells. FIG. 6 shows non-transfected control cells without primary antibody (C and D, infected cells, n=1.1×10$^5$, pdl=3.8, passage 2).

Figure 7:
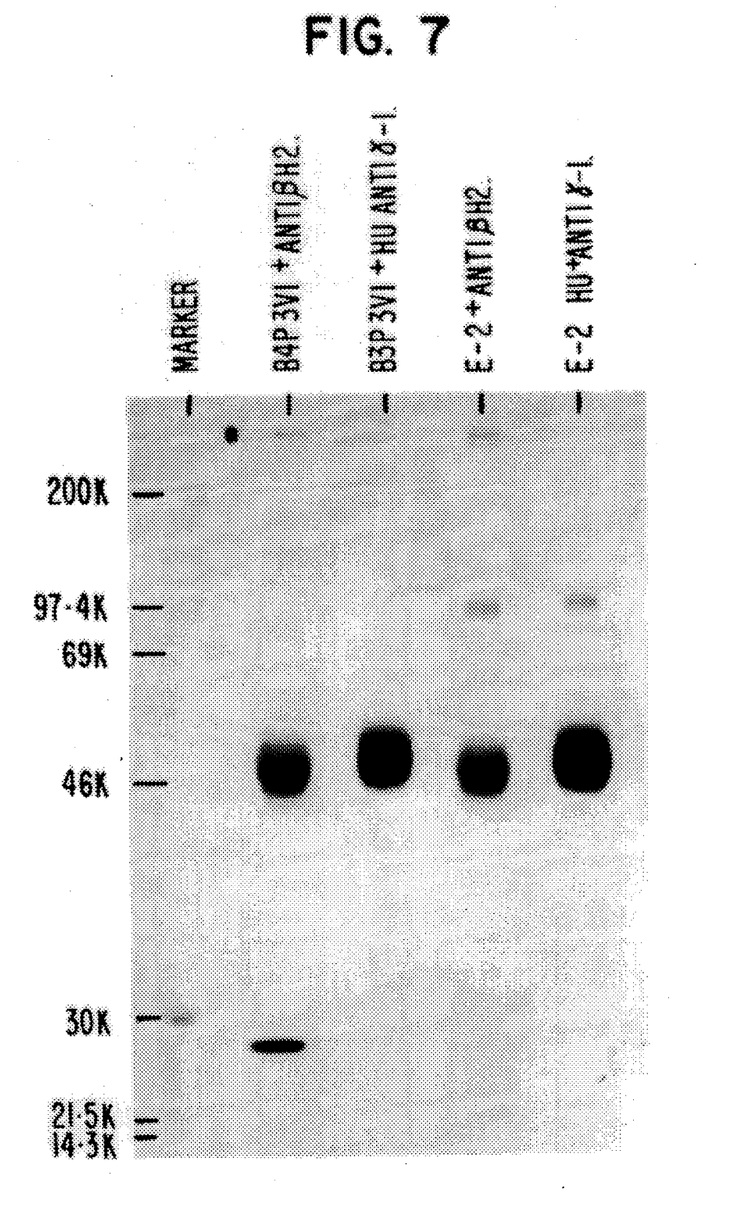
FIGS. 7 and 8 are an analysis of protein from cultured immortal cells.
Figure 8:
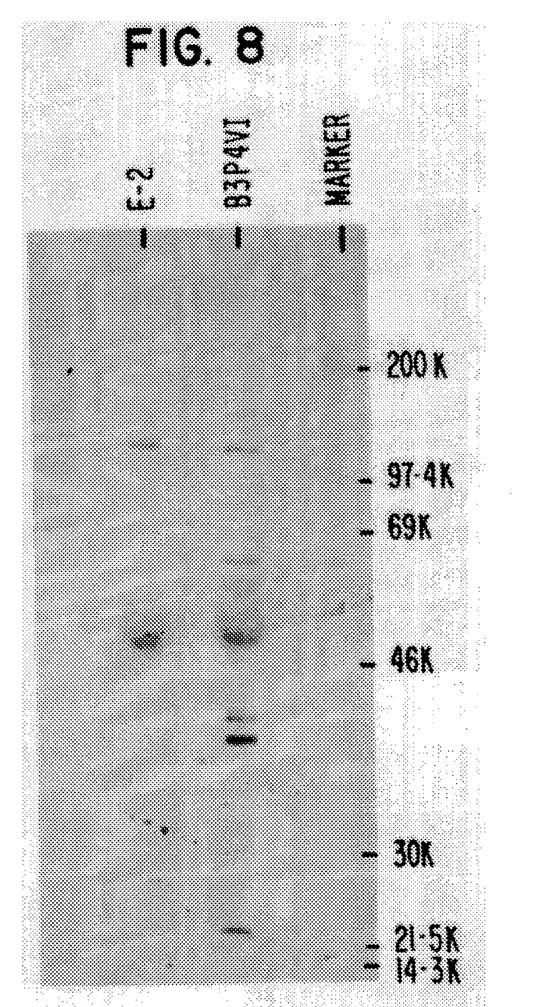

In FIGS. 7 and 8, the analyses of proteins by SDS-PAGE and Western blotting showed that the immortalized cells produce proteins of molecular weights between 20–30 kD, which react with the antibodies to βH- and γ-crystallins proteins that are markers for cell differentiation in the lens epithelium. The Figures depict the following lanes: lane 1, molecular weight markers; lane 2, cells in the third passage after virus infection immunoblotted with an antibody to calf lens βH-crystallin; lane 3, cells in passage 3 (pdl=9.9) after virus infection immunoblotted with an antibody against infant human lens γ-crystallin; lane 4, human corneal fibroblast cells as a control immunoblotted with βH-crystallin antibody; lane 5, human corneal fibroblast cells as a control immunoblotted with an antibody to human lens γ-crystallin; lane 6, human lens epithelial cells in passage 17 immunoblotted with antibody βH-crystallin (pd1=38.6).

The invention being thus described, it will be obvious that the same may be varied in many ways. Such variations are not to be regarded as a departure from the spirit and scope of the invention, and all such modifications are intended to be included within the scope of the following claims.

What is claimed is:

1. An immortalized human lens epithelial cell line, which comprises: a human lens epithelial cell line ATCC CRL 11421 infected with hybrid adenovirus Ad12-SV40 which propagates the immortalized cell line in vitro, wherein the immortalized cell line produces a β-crystallin.

2. The immortalized cell line of claim 1, wherein the immortalized cell line produces a β-crystallin having a molecular weight of between 20–30 kD.

3. The immortalized cell line of claim 1, wherein the immortalized cell line produces β5-crystallin.

4. The immortalized cell line of claim 1, wherein the immortalized cell line produces a β-crystallin having a molecular weight of 24 kD.

5. A human lens epithelial cell culture that expresses a β-crystallin, wherein the cell culture is obtained by infecting human lens epithelial cells having all the identifying characteristics of cell line ATCC CRL 11421 with Ad12-SV40.

6. A cell line having all the identifying characteristics of cell line ATCC CRL 11421.

7. A method for producing an immortalized human lens epithelial cell line, which comprises the steps of:
   (a) culturing a human lens epithelial cell line having all the identifying characteristics of cell line ATCC CRL 11421 with hybrid adenovirus Ad12-SV40 to infect the cell line and to form an immortalized cell line capable of propagating in vitro; and
   (b) collecting the immortalized cell line.

8. The method of claim 7, wherein the immortalized cell line produces β-crystallins.

* * * * *